US012616536B2

(12) United States Patent
Keret et al.

(10) Patent No.: US 12,616,536 B2
(45) Date of Patent: May 5, 2026

(54) ROBOTIC SURGICAL SYSTEM WITH FLOATING PATIENT MOUNT

(71) Applicant: Mazor Robotics Ltd., Caesarea (IL)

(72) Inventors: Amir Keret, Atlit (IL); Ziv Seemann, Beit Ytzhack (IL); Nimrod Dori, Atlit (IL); Ron Visbrot, Hadera (IL); Adi Sandelson, Givatayim (IL); Dvir Kadshai, Tel Aviv (IL)

(73) Assignee: Mazor Robotics Ltd., Caesarea (IL)

( * ) Notice: Subject to any disclaimer, the term of this patent is extended or adjusted under 35 U.S.C. 154(b) by 652 days.

(21) Appl. No.: 17/734,913

(22) Filed: May 2, 2022

(65) Prior Publication Data

US 2023/0346492 A1 Nov. 2, 2023

(51) Int. Cl.
| | |
|---|---|
| *A61B 34/32* | (2016.01) |
| *A61B 34/00* | (2016.01) |
| *B25J 9/00* | (2006.01) |
| *B25J 9/16* | (2006.01) |
| *B25J 13/08* | (2006.01) |
| *B25J 15/04* | (2006.01) |

(52) U.S. Cl.
CPC .............. *A61B 34/32* (2016.02); *A61B 34/77* (2016.02); *B25J 9/0009* (2013.01); *B25J 9/162* (2013.01); *B25J 9/1633* (2013.01); *B25J 13/085* (2013.01); *B25J 13/089* (2013.01); *B25J 15/04* (2013.01)

(58) Field of Classification Search
CPC ........ A61B 34/32; A61B 34/77; B25J 9/0009; B25J 9/162; B25J 9/1633; B25J 13/085; B25J 13/089; B25J 15/04
See application file for complete search history.

(56) References Cited

U.S. PATENT DOCUMENTS

| | | | |
|---|---|---|---|
| 4,870,592 | A | 9/1989 | Lampi et al. |
| 5,343,391 | A | 8/1994 | Mushabac |

(Continued)

FOREIGN PATENT DOCUMENTS

| | | |
|---|---|---|
| KR | 10-2017-0091588 | 8/2017 |
| WO | WO 2004/096502 | 11/2004 |

(Continued)

OTHER PUBLICATIONS

International Search Report for PCT/IL2023/050437 date of completion is Aug. 14, 2023 (16 pages).

*Primary Examiner* — Erin Mcgrath
(74) *Attorney, Agent, or Firm* — Sheridan Ross P.C.

(57) ABSTRACT

A system includes a robot mounted to a movable base, the robot including one or more robotic arms. The system monitors, by one or more measurement devices, one or more parameters associated with an object. The system adjusts a pose of the robot based on the one or more parameters satisfying one or more criteria. The system outputs an alert based on the one or more parameters satisfying one or more second criteria. The system performs a registration process associated with the object and the robot, based on the one or more parameters satisfying the one or more second criteria. The one or more measurement devices include a mechanical measurement device that maintains a non-rigid connection between the robot and the object. The one or more measurement devices include an optical measurement device, an acoustic transducer, or a multi-sensor device.

14 Claims, 6 Drawing Sheets

(56) References Cited

U.S. PATENT DOCUMENTS

| | | | |
|---|---|---|---|
| 6,033,415 | A | 3/2000 | Mittelstadt et al. |
| 6,322,567 | B1 | 11/2001 | Mittelstadt et al. |
| 6,430,434 | B1 | 8/2002 | Mittelstadt |
| 6,788,018 | B1 | 9/2004 | Blumenkranz |
| 8,400,094 | B2 | 3/2013 | Schena |
| 10,391,635 | B2 | 8/2019 | Berghofer et al. |
| 10,842,461 | B2 | 11/2020 | Johnson et al. |
| 2005/0234327 | A1 | 10/2005 | Saracen et al. |
| 2009/0080737 | A1 | 3/2009 | Battle et al. |
| 2009/0314925 | A1 | 12/2009 | Van Vorhis et al. |
| 2012/0085934 | A1 | 4/2012 | Marcelis et al. |
| 2013/0096574 | A1 | 4/2013 | Kang et al. |
| 2014/0264657 | A1* | 9/2014 | Gogoi ..................... H01L 27/14 257/415 |
| 2015/0335480 | A1 | 11/2015 | Alvarez et al. |
| 2016/0310221 | A1* | 10/2016 | Bar ........................ A61B 90/06 |
| 2018/0185100 | A1 | 7/2018 | Weinstein et al. |
| 2019/0038268 | A1 | 2/2019 | Kopp |
| 2019/0090800 | A1 | 3/2019 | Bosworth et al. |
| 2019/0201146 | A1* | 7/2019 | Shelton, IV ..... A61B 17/07207 |
| 2019/0206565 | A1 | 7/2019 | Shelton, IV |
| 2020/0069376 | A1 | 3/2020 | Garcia et al. |
| 2020/0129241 | A1 | 4/2020 | Forstein et al. |
| 2020/0188032 | A1 | 6/2020 | Komp et al. |
| 2020/0281742 | A1 | 9/2020 | Wu et al. |
| 2020/0315737 | A1 | 10/2020 | Crawford et al. |
| 2020/0384287 | A1 | 12/2020 | Hetz |
| 2021/0145523 | A1 | 5/2021 | Xing et al. |
| 2021/0169582 | A1 | 6/2021 | Li et al. |
| 2021/0275260 | A1 | 9/2021 | Kang et al. |
| 2021/0322032 | A1 | 10/2021 | Gogarty et al. |
| 2022/0096188 | A1 | 3/2022 | Ellman et al. |

FOREIGN PATENT DOCUMENTS

| | | |
|---|---|---|
| WO | WO 2004/100812 | 11/2004 |
| WO | WO 2008/094766 | 8/2008 |
| WO | WO 2010/068005 | 6/2010 |
| WO | WO 2010/068213 | 6/2010 |
| WO | WO 2015/087335 | 6/2015 |
| WO | WO 2017/122202 | 7/2017 |
| WO | WO 2018/053282 | 3/2018 |
| WO | WO 2020/181076 | 9/2020 |
| WO | WO 2020/185930 | 9/2020 |
| WO | WO 2021/011280 | 1/2021 |
| WO | WO 2021/062001 | 4/2021 |
| WO | WO 2021/219502 | 11/2021 |

* cited by examiner 200-a

201

242

216

238

250-b

246

250-a

208

204

226

212 d1 d2

202

Z

X

Y 200-b

201

242

214

216

240-a

246

254

208 d1

212

204

226

202

Z

X

Y

ROBOTIC SURGICAL SYSTEM WITH FLOATING PATIENT MOUNT

FIELD

The present disclosure is generally directed to surgical systems, and relates more particularly to robotic surgical devices.

BACKGROUND

Surgical robots may assist a surgeon or other medical provider in carrying out a surgical procedure, or may complete one or more surgical procedures autonomously. Providing controllable linked articulating members allows a surgical robot to reach areas of a patient anatomy during various medical procedures.

BRIEF SUMMARY

Example Aspects of the Present Disclosure Include

A system including: a robot mounted to a movable base, the robot including one or more robotic arms; one or more measurement devices; a processor; and memory in electronic communication with the processor; and instructions stored in the memory, the instructions being executable by the processor to: monitor, by the one or more measurement devices, one or more parameters associated with an object; and adjust a pose of the robot based on the one or more parameters satisfying one or more criteria.

Any of the aspects herein, wherein adjusting the pose of the robot includes at least one of: adjusting a position of the robot or a position of the one or more robotic arms; and adjusting an orientation of the robot or an orientation of the one or more robotic arms, or both.

Any of the aspects herein, wherein the instructions are further executable by the processor to at least one of: output an alert based on the one or more parameters satisfying one or more second criteria; and perform a registration process associated with the object and the robot, based on the one or more parameters satisfying the one or more second criteria.

Any of the aspects herein, wherein the one or more parameters include at least one of movement information, positional information, and orientation information associated with the object.

Any of the aspects herein, wherein: the one or more parameters include positional information associated with the object; and the one or more criteria include a displacement threshold with respect to reference positional information associated with the object.

Any of the aspects herein, wherein the one or more measurement devices include a mechanical measurement device coupled to the robot and the object.

Any of the aspects herein, wherein the mechanical measurement device maintains a non-rigid connection between the robot and the object.

Any of the aspects herein, wherein: the mechanical measurement device includes one or more coupling elements configured to detach based on at least one of: a first force value measured at the object, a second force value measured at a portion of the mechanical measurement device, or both; and a displacement value of the object exceeding a threshold displacement value, wherein the displacement value is measured by the mechanical measurement device.

Any of the aspects herein, wherein the one or more measurement devices include one or more optical measurement devices, wherein the one or more optical measurement devices are coupled to the robot, the one or more robotic arms, or both.

Any of the aspects herein, wherein the one or more measurement devices include at least one of: a first acoustic transducer coupled to the robot or the one or more robotic arms; and a second acoustic transducer coupled to the object.

Any of the aspects herein, wherein the one or more measurement devices include a multi-sensor device coupled to the object.

Any of the aspects herein, wherein the multi-sensor device is a monolithic integrated multi-sensor (MIMS) device including at least one of: a gyroscope; and an accelerometer.

Any of the aspects herein, wherein the object includes an anatomical element.

An apparatus including: a robot, the robot including one or more robotic arms; a movable base coupled to the robot; one or more measurement devices; a processor; and memory in electronic communication with the processor; and instructions stored in the memory, the instructions being executable by the processor to: monitor, by the one or more measurement devices, one or more parameters associated with an object; and adjust a pose of the robot based on the one or more parameters satisfying one or more criteria.

Any of the aspects herein, wherein the one or more measurement devices include a mechanical measurement device coupled to the robot and the object.

Any of the aspects herein, wherein the mechanical measurement device maintains a non-rigid connection between the robot and the object.

Any of the aspects herein, wherein the mechanical measurement device includes one or more coupling elements configured to detach based on at least one of: a first force value measured at the object, a second force value measured at a portion of the mechanical measurement device, or both; and a displacement value of the object exceeding a threshold displacement value, wherein the displacement value is measured by the mechanical measurement device.

Any of the aspects herein, wherein the one or more measurement devices include at least one of: one or more optical measurement devices, wherein the one or more optical measurement devices are coupled to the robot, the one or more robotic arms, or both; one or more acoustic transducers, wherein the one or more acoustic transducers are coupled to the robot, the one or more robotic arms, the object, or a combination thereof; and a multi-sensor device coupled to the object.

A method including: monitoring, by one or more measurement devices of a robot, one or more parameters associated with an object; and adjusting a pose of the robot based on the one or more parameters satisfying one or more criteria, wherein the robot is mounted to a movable base.

Any of the aspects herein, further including: outputting an alert based on the one or more parameters satisfying one or more second criteria; and performing a registration process associated with the object and the robot, based on the one or more parameters satisfying the one or more second criteria.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/implementations in combination with any one or more other aspects/features/implementations.

Use of any one or more of the aspects or features as disclosed herein.

It is to be appreciated that any feature described herein can be claimed in combination with any other feature(s) as described herein, regardless of whether the features come from the same described implementation.

The details of one or more aspects of the disclosure are set forth in the accompanying drawings and the description below. Other features, objects, and advantages of the techniques described in this disclosure will be apparent from the description and drawings, and from the claims.

The preceding is a simplified summary of the disclosure to provide an understanding of some aspects of the disclosure. This summary is neither an extensive nor exhaustive overview of the disclosure and its various aspects, implementations, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, implementations, and configurations of the disclosure are possible utilizing, alone or in combination, one or more of the features set forth above or described in detail below.

Numerous additional features and advantages of the present disclosure will become apparent to those skilled in the art upon consideration of the implementation descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, implementations, and configurations of the disclosure, as illustrated by the drawings referenced below.

DETAILED DESCRIPTION

Figure 1:
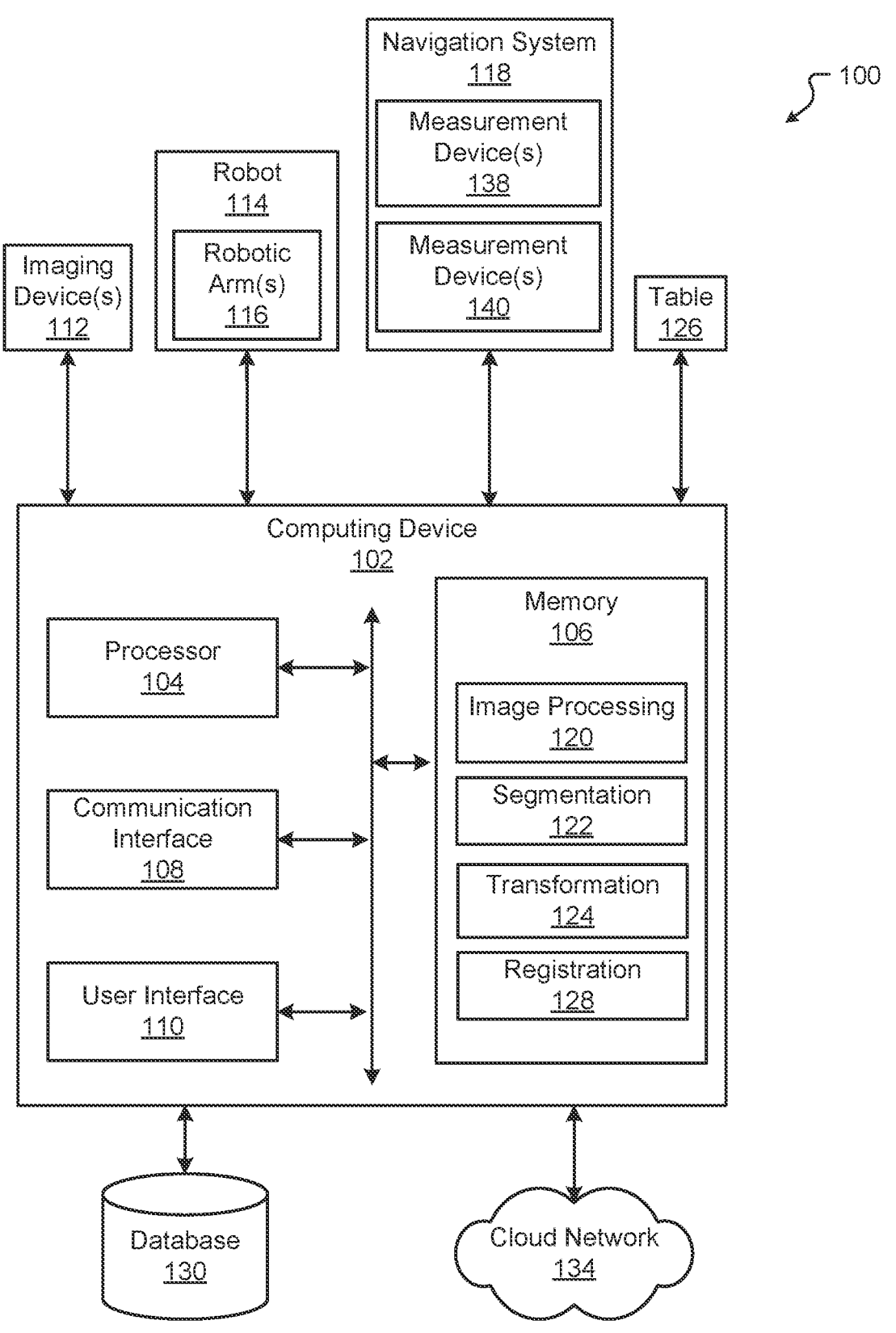
FIG. 1 is a block diagram of a system according to at least one implementation of the present disclosure.

It should be understood that various aspects disclosed herein may be combined in different combinations than the combinations specifically presented in the description and accompanying drawings. It should also be understood that, depending on the example or implementation, certain acts or events of any of the processes or methods described herein may be performed in a different sequence, and/or may be added, merged, or left out altogether (e.g., all described acts or events may not be necessary to carry out the disclosed techniques according to different implementations of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any implementations of the disclosure are explained in detail, it is to be understood that the disclosure is not limited in its application to the details of construction and the arrangement of components set forth in the following description or illustrated in the drawings. The disclosure is capable of other implementations and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Some robotic system implementations include mounting a robotic system to a surgical table (e.g., a surgical bed, an operating table, etc.) and to a patient (e.g., a robot is mounted to a patient such that the patient's body supports the weight of the robot). Such table-mounted and patient-mounted implementations may provide increased accuracy compared to other robotic system implementations in which a robot is not mounted to the patient. The term "robotic system" may also be referred to as a "robotic surgical system" herein.

In some table-mounted robotic system implementations, weight limitations associated with a surgical table may impact the total allowable weight of the robotic system. For example, a surgical table may have a weight limit. Accordingly, for example, the weight of a patient and the weight limit of the surgical table may impact (e.g., limit) the total weight of the robotic system.

Further, in some robotic system implementations (e.g., in which the robotic system is not table-mounted or patient-mounted), movement of the robotic system during a surgical operation may result in movement (e.g., in any direction) of the surgical table. In some cases, the movement of the surgical table may result in malfunction of the robotic system, for example, in association with object tracking (e.g., tracking the patient, tracking anatomical elements of the patient, etc.). In some other cases, the movement of the surgical table relative to the robotic sysrobotic system may result in a loss of synchronization between a coordinate system of the robot (e.g., a robotic arm) and a coordinate system associated with the patient or the surgical table. For example, the movement of the surgical table may result in a new registration process with respect to the patient (e.g., patient anatomy, patient body, etc.) and components of the robotic system (e.g., robot, robotic arm, end effector of the robotic arm, etc.).

Aspects of the present disclosure support a robotic system with a floating patient mount. In an example, the robotic system may be mounted to a workstation (e.g., a mobile cart) separate from a surgical table. Example techniques of the present disclosure may support providing accurate position feedback of the patient relative to the robotic system, for example, while the robot is mounted to the workstation.

Aspects of the robotic system may support monitoring of patient movement in absolute terms as well as relative to one or more landmarks or objects of interest. For example, the robotic system may monitor patient movement based on tracking information, positional information, and/or image data associated with the patient. In an example, the robotic system may monitor patient movement with respect to a robot(s), a robotic arm(s), and/or a surgical tool controlled by the workstation.

In some aspects, the robotic system may utilize the patient movement information in association with positioning a robotic arm and/or an end effector of the robotic arm. For example, the robotic system may correct movement of the end effector in accordance with the patient movement information (e.g., correct the end effector location) so as to maintain a target accuracy with respect to positioning or movement of the end effector. In some aspects, the robotic system may correct the movement of the robotic arm and/or the end effector when a displacement between a reference position of a tracked object (e.g., an anatomical element) and a measured position of the tracked object exceeds a first threshold displacement value. In some examples, the patient movement information may be vectorial. For example, the robotic system may support monitoring patient movement and controlling the robotic arm (and/or end effector of the robotic arm) according to multiple degrees of freedom (e.g., six degrees-of-freedom (DoF)).

In some aspects, the robotic system may initiate a new registration process for cases in which a relatively large movement (e.g., of the patient, of the surgical table, etc.) exceeds a second threshold displacement value (e.g., higher than the first threshold displacement value). For example, if the robotic system detects that a movement (e.g., of the patient, of the surgical table, etc.) exceeds the second threshold displacement value, the robotic system may generate and output an alert (e.g., an audio, visual, and/or haptic notification) indicating the need for a new registration process.

In some aspects, the second threshold displacement value may be based on (e.g., equal to, less than) a displacement between the reference position of the tracked object (e.g., an anatomical element) and a measured position of the tracked object that results in a loss of registration between the robotic system and the tracked object. In an example, the robotic system may perform a new registration process when the second threshold displacement value is exceeded. For example, the new registration process may include registering coordinate systems of the robotic system to a coordinate system associated with the tracked object. In an example, the registration process may yield a correlation between a patient-based coordinate system and a coordinate system of a navigation system associated with the robotic system. The robotic system may generate and output an alert (e.g., audible, visual, haptic, etc.) or notification when the first threshold displacement value and/or the second threshold displacement value is exceeded.

The robotic system may include a mechanical arm coupled (e.g., mechanically, electrically, directly, and/or indirectly) to the workstation. In an example, the mechanical arm may be mechanically and electrically coupled to the workstation. In another example, the mechanical arm may be mechanically separate from the workstation, but electrically coupled to the workstation (e.g., in association with receiving and transmitting data and/or signals). In some other examples, the mechanical arm may be mechanically and electrically separate from the workstation, but controlled (e.g., using wireless communications) by the workstation.

The mechanical arm may be separate from a robotic arm (e.g., a surgical arm) coupled to the workstation. In some aspects, the mechanical arm may include one or more components supportive of bending, flexion, and/or movement of the mechanical arm. The mechanical arm may freely bend and/or move (e.g., via bending at one or more joints or articulation points of the mechanical arm) in association with maintaining the non-rigid connection. The mechanical arm may provide relatively minimal resistance (e.g., below a threshold resistance) supportive of the bending, flexion, and/or movement. The mechanical arm may support or maintain a non-rigid connection between the robot and the patient. The mechanical arm may support coordinate measuring and coordinate tracking in association with the patient (e.g., an anatomical element of the patient).

In some aspects, the mechanical arm may be a high accuracy mechanical measurement device based on the robot. The mechanical arm may be attached to the patient, for example, via a clamp, a pin, a rod, a screw (e.g., Schanz screw), or the like. In some aspects, the mechanical arm may part of a portable, coordinate measuring machine that supports precise and accurate measurements of an object (e.g., an anatomical element of the patient).

The mechanical arm may support features for automatically disconnecting from the patient based on a set of criteria. For example, the mechanical arm may include one or more coupling elements (also referred to herein as mechanical attachments) capable of automatically disconnecting from the patient based on the set of criteria. Additionally, or alternatively, the coupling elements may be capable of disconnecting from each other based on the set of criteria.

In an example, a coupling element of the mechanical arm may detach (e.g., disconnect) from another coupling element of the mechanical arm when a measured force (e.g., exerted on the patient, sensed at the mechanical arm, etc.) exceeds a threshold force value. Additionally, or alternatively, the coupling element may automatically detach (e.g., disconnect) from the other coupling element when a displacement (e.g., between the robotic system and the object) exceeds a threshold displacement value. In some aspects, the threshold displacement value may be based on (e.g., equal to, less than) a maximum extendable length of the mechanical arm.

In an alternative or additional example, the coupling element may detach (e.g., disconnect) from a point of attachment (e.g., a clamp, a pin, a rod, a screw (e.g., Schanz screw), etc.) to the object when the measured force exceeds the threshold force value or when the displacement (e.g., between the robotic system 201 and the anatomical element 208) exceeds the threshold displacement value. In an example, the robotic system may generate and output an alert (e.g., audible, visual, haptic, etc.) or notification when the threshold force value is exceeded, the threshold displacement is exceeded, and/or the mechanical attachment becomes disconnected.

In some alternative and/or additional aspects, the robotic system may include a high accuracy optical measurement device based on the robot. The optical measurement device may be attached to the patient, for example, via a clamp, a pin, a rod, a screw (e.g., Schanz screw), or the like. In an example, the optical measurement device may include one or more cameras (e.g., tracking cameras, imaging cameras, depth cameras, etc.), one or more laser tracking devices, or the like.

In some aspects, the robotic system may include a high accuracy acoustic measurement device based on the robot. In an example, the acoustic measurement device may include an ultrasonic sensor capable of tracking coordinates, position, and/or movement of a coupling element (e.g., a Schanz screw) attached to a tracked object (e.g., anatomical element). The ultrasonic sensor may include an acoustic transducer capable of transmitting and receiving ultrasonic signals (e.g., ultrasonic pulses). In an example, based on ultrasonic signals received from (e.g., reflected from) the coupling element (or the anatomical element), the acoustic measurement device may determine or calculate coordinates, position, and/or movement of the coupling element and the anatomical element).

In some aspects, the robotic system may include a measurement device capable of providing high accuracy acceleration measurements and/or rotational measurements. The measurement device may be attached to the patient, for example, via a clamp, a pin, a rod, a screw (e.g., Schanz screw), or the like. In an example, the measurement device may include an accelerometer. In another example, the measurement device may include a gyroscope. In some aspects, the measurement device may be a monolithic integrated multi-sensor (MIMS) device including a combination of sensors (e.g., an indirect interface sensor such as an accelerometer or gyroscope, a direct interface sensor such as a microphone, etc.).

Implementations of the present disclosure provide technical solutions to one or more of the problems of weight limitations in some table mounted robotic systems (e.g., bed mounted robotic systems). For example, aspects of the floating patient mount described herein support implementations in which robotic arms are mounted to a mobile base (e.g., a mobile cart, a mobile workstation, etc.) separate from a surgical table, rather than being mounted to the surgical table. Accordingly, for example, features and resultant weights of the robotic arms and the surgical tools are not impacted by the weight limit of a surgical table. Aspects of the robotic system described herein support robotic arms and surgical tools that are more robust and heavier compared to robotic arms and surgical tools associated with table mounted robotic systems. In some other aspects, as the robotic arms are not mounted to the surgical table, the surgical table may support an increased amount of weight related to patients (e.g., support obese patients).

In some aspects, aspects of the mechanical arm (e.g., non-rigid connection) and/or optical implementations described with reference to tracking patient movement and patient positioning (e.g., anatomical element position) may support a reduced amount of pressure applied to the patient compared to some other robotic systems.

Further, aspects of the robotic system associated with generating a corresponding alert and/or performing a new registration process when a detected movement (e.g., of the patient, of the surgical table, etc.) exceeds a threshold value may improve process safety. For example, generating the alert and/or performing a new registration process may improve patient safety (e.g., maintain accuracy of a surgical robot) in association with a surgical procedure.

FIG. 1 illustrates an example of a system 100 that supports aspects of the present disclosure.

The system 100 includes a computing device 102, imaging devices 112, a robot 114, a navigation system 118, a table 126, a database 130, and/or a cloud network 134 (or other network). Systems according to other implementations of the present disclosure may include more or fewer components than the system 100. For example, the system 100 may omit and/or include additional instances of the computing device 102, imaging devices 112, the robot 114, the navigation system 118, measurement device 138, measurement device 140, the table 126, one or more components of the computing device 102, the database 130, and/or the cloud network 134. The system 100 may support the implementation of one or more other aspects of one or more of the methods disclosed herein.

The computing device 102 includes a processor 104, a memory 106, a communication interface 108, and a user interface 110. Computing devices according to other implementations of the present disclosure may include more or fewer components than the computing device 102. The computing device 102 may be, for example, a control device including electronic circuitry associated with controlling the imaging devices 112, the robot 114, the navigation system 118, and the table 126.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from imaging devices 112, the robot 114, the navigation system 118, the table 126, the database 130, and/or the cloud network 134.

The memory 106 may be or include RAM, DRAM, SDRAM, other solid-state memory, any memory described herein, or any other tangible, non-transitory memory for storing computer-readable data and/or instructions. The memory 106 may store information or data associated with completing, for example, any step of the method 400 described herein, or of any other methods. The memory 106 may store, for example, instructions and/or machine learning models that support one or more functions the computing device 102, imaging devices 112, the robot 114, the navigation system 118, the table 126. For instance, the memory 106 may store content (e.g., instructions and/or machine learning models) that, when executed by the processor 104, enable image processing 120, segmentation 122, transformation 124, and/or registration 128). Such content, if provided as in instruction, may, in some implementations, be organized into one or more applications, modules, packages, layers, or engines. Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging devices 112, the robot 114, the navigation system 118, the database 130, and/or the cloud network 134. measurement device(s) 138

The computing device 102 may also include a communication interface 108. The communication interface 108 may be used for receiving data or other information from an external source (e.g., the imaging devices 112, the robot 114, the navigation system 118, the database 130, the cloud network 134, and/or any other system or component separate from the system 100), and/or for transmitting instructions, data (e.g., image data provided by the imaging devices 112, measurement data provided by measurement device(s) 138, measurement device(s) 140, etc.), or other information to an external system or device (e.g., another computing device 102, the imaging devices 112, the robot 114, the navigation system 118, the database 130, the cloud network 134, and/or any other system or component not part of the system 100). The communication interface 108 may include one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some implementations, the communication interface 108 may support communication between the device 102 and one or more other processors 104 or computing devices 102, whether to reduce the time needed to accomplish a computing-intensive task or for any other reason.

The computing device 102 may also include one or more user interfaces 110. The user interface 110 may be or include a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some implementations, the user interface 110 may support user modification (e.g., by a surgeon, medical personnel, a patient, etc.) of instructions to be executed by the processor 104 according to one or more implementations of the present disclosure, and/or to user modification or adjustment of a setting of other information displayed on the user interface 110 or corresponding thereto.

In some implementations, the computing device 102 may utilize a user interface 110 that is housed separately from one or more remaining components of the computing device 102. In some implementations, the user interface 110 may be located proximate one or more other components of the computing device 102, while in other implementations, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some implementations, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some implementations, the imaging device 112 may comprise more than one imaging device 112. For example, a first imaging device may provide first image data and/or a first image, and a second imaging device may provide second image data and/or a second image. In still other implementations, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some implementations, the robot 114 may be configured to hold and/or manipulate an anatomical element during or in connection with a surgical procedure. The robot 114 may be configured to operate or control aspects of a measurement device 138 and/or a measurement device 140 described herein.

The robot 114 may comprise one or more robotic arms 116. In some implementations, the robotic arm 116 may comprise a first robotic arm and a second robotic arm, though the robot 114 may comprise more than two robotic arms. In some implementations, one or more of the robotic arms 116 may be used to hold and/or maneuver the imaging device 112. In implementations where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more DoF. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm). The robotic arm(s) 116 may include an end effector (not illustrated) coupled to a distal end of the robotic arm(s). The end effector may support interaction of the robotic arm(s) with an environment.

In some implementations, reference markers (e.g., navigation markers, three-dimensional markers) may be placed on the robot 114 (including, e.g., on the robotic arm 116), the imaging device 112, the measurement device(s) 138, the measurement device(s) 140, the table 126, or any other object in the surgical space. The reference markers may be tracked by the navigation system 118, and the results of the tracking may be used by the robot 114 and/or by an operator of the system 100 or any component thereof. In some implementations, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some implementations, the navigation system 118 may comprise one or more electromagnetic sensors. In various implementations, the navigation system 118 may be used to track a position and orientation (e.g., a pose) of the imaging device 112, the robot 114 and/or robotic arm 116, the measurement device(s) 138, the measurement device(s) 140, and/or one or more surgical tools (or, more particularly, to track a pose of a navigated tracker attached, directly or indirectly, in fixed relation to the one or more of the foregoing).

The system 100 may support a non-rigid connection between the robot 114 and a patient implemented, for example, using the measurement device(s) 138. The measurement device(s) 138 may support coordinate measuring and coordinate tracking in association with the patient (e.g., an anatomical element of the patient). In an example, the measurement device(s) 138 may be a mechanical arm coupled to a workstation or the robot 114 (later illustrated at FIG. 2A) and an object (e.g., anatomical element of a patient). In some aspects, the workstation may include the computing device 102. The measurement device(s) 138 may also be referred to herein as a mechanical measurement device(s) 138. Example aspects of the measurement device(s) 138 are later described herein with reference to FIG. 2A.

The system 100 may support alternative and/or additional implementations of coordinate measuring and coordinate tracking in association with the patient (e.g., an anatomical element of the patient) using the measurement device(s) 140. In an example, the measurement device(s) 140 may be coupled to a workstation or the robot 114 (later illustrated at FIG. 3) and/or an object (e.g., an anatomical element of a patient). In an example, the measurement device(s) 140 may include an optical measurement device(s), an acoustic measurement device(s) (e.g., an acoustic transducer), and/or a measurement device(s) capable of providing acceleration measurements and/or rotational measurements, aspects of which are later described with reference to FIGS. 2B through 2D. In some aspects, the measurement device(s) 140 may include a multi-sensor device such as, for example, an MIMS device. In some aspects, the measurement device(s) 140 may be a gyroscope, an accelerometer, or the like.

The navigation system 118 may include a display (e.g., display 242 later described herein) for displaying one or more images from an external source (e.g., the computing device 102, imaging device 112, or other source) or for displaying an image and/or video stream from the one or more cameras or other sensors of the navigation system 118. In some implementations, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may additionally or alternatively store, for example, location or coordinates of objects (e.g., anatomical elements of a patient) associated with the system 100. The database 130 may be configured to provide any such information to the computing device 102 or to any other device of the system 100 or external to the system 100, whether directly or via the cloud network 134.

In some implementations, the database 130 may include thresholds associated with movement of a patient, the robot 114, the measurement device(s) 138, the measurement device(s) 140, and/or the table 126.

For example, the database 130 may include thresholds associated with a force value measured at an object (e.g., anatomical element of the patient). The database 130 may include thresholds associated with a force value measured at the measurement device(s) 138 (e.g., a mechanical measurement device, such as a mechanical arm described herein). The force values (e.g., at the object, at the measurement device(s) 138, etc.) may be measured and/or calculated by any combination of the measurement device(s) 138, the robot 114, the navigation system 118, and the computing device 102. The thresholds may be set or modified, for example, by the computing device 102.

In some aspects, the database 130 may include thresholds associated with a displacement value of the object (e.g., anatomical element) with respect to reference positional information associated with the object. In some aspects, the displacement value may be measured and/or calculated based on data measured using the measurement device(s) 138 (e.g., a mechanical measurement device). Additionally, or alternatively, the displacement value may be measured and/or calculated based on data measured using the measurement device(s) 140 (e.g., optical measurement devices, acoustic transducers, multi-sensor devices, MIMS devices, gyroscope, accelerometer, etc.)

In some implementations, the database 130 may be or comprise part of a hospital image storage system, such as a picture archiving and communication system (PACS), a health information system (HIS), and/or another system for collecting, storing, managing, and/or transmitting electronic medical records including image data.

In some aspects, the computing device 102 may communicate with a server(s) and/or a database (e.g., database 130) directly or indirectly over a communications network (e.g., the cloud network 134). The communications network may include any type of known communication medium or collection of communication media and may use any type of protocols to transport data between endpoints. The communications network may include wired communications technologies, wireless communications technologies, or any combination thereof.

Wired communications technologies may include, for example, Ethernet-based wired local area network (LAN) connections using physical transmission mediums (e.g., coaxial cable, copper cable/wire, fiber-optic cable, etc.). Wireless communications technologies may include, for example, cellular or cellular data connections and protocols (e.g., digital cellular, personal communications service (PCS), cellular digital packet data (CDPD), general packet radio service (GPRS), enhanced data rates for global system for mobile communications (GSM) evolution (EDGE), code division multiple access (CDMA), single-carrier radio transmission technology (1×RTT), evolution-data optimized (EVDO), high speed packet access (HSPA), universal mobile telecommunications service (UMTS), 3G, long term evolution (LTE), 4G, and/or 5G, etc.), Bluetooth®, Bluetooth® low energy, Wi-Fi, radio, satellite, infrared connections, and/or ZigBee® communication protocols.

The Internet is an example of the communications network that constitutes an Internet Protocol (IP) network consisting of multiple computers, computing networks, and other communication devices located in multiple locations, and components in the communications network (e.g., computers, computing networks, communication devices) may be connected through one or more telephone systems and other means. Other examples of the communications network may include, without limitation, a standard Plain Old Telephone System (POTS), an Integrated Services Digital Network (ISDN), the Public Switched Telephone Network (PSTN), a Local Area Network (LAN), a Wide Area Network (WAN), a wireless LAN (WLAN), a Session Initiation Protocol (SIP) network, a Voice over Internet Protocol (VoIP) network, a cellular network, and any other type of packet-switched or circuit-switched network known in the art. In some cases, the communications network 120 may include of any combination of networks or network types. In some aspects, the communications network may include any combination of communication mediums such as coaxial cable, copper cable/wire, fiber-optic cable, or antennas for communicating data (e.g., transmitting/receiving data).

The computing device 102 may be connected to the cloud network 134 via the communication interface 108, using a wired connection, a wireless connection, or both. In some implementations, the computing device 102 may communicate with the database 130 and/or an external device (e.g., a computing device) via the cloud network 134.

The system 100 or similar systems may be used, for example, to carry out one or more aspects of the process flow 300 described herein. The system 100 or similar systems may also be used for other purposes.

Aspects of the system 100 supportive of monitoring patient movement are later described herein with reference to the following figures.

Referring to FIGS. 2A through 2D, examples 200-*a* through 200-*d* of a robotic system 201 and components thereof are shown according example implementations of the present disclosure.

Features of the robotic system 201 may be described in conjunction with a coordinate system 202. The coordinate system 202, as shown in FIGS. 2A through 2D, includes three-dimensions comprising an X-axis, a Y-axis, and a Z-axis. Additionally or alternatively, the coordinate system 202 may be used to define planes (e.g., the XY-plane, the XZ-plane, and the YZ-plane) of the robotic system 201. These planes may be disposed orthogonal, or at 90 degrees, to one another. While the origin of the coordinate system 202 may be placed at any point on or near the components of the robotic system 201, for the purposes of description, the axes of the coordinate system 202 are always disposed along the same directions from figure to figure, whether the coordinate system 202 is shown or not. In some examples, reference may be made to dimensions, angles, directions, relative positions, and/or movements associated with one or more components of the robotic system 201 with respect to the coordinate system 202.

Figure 2A:
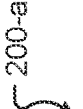
FIGS. 2A through 2D illustrate examples of a system according to at least one implementation of the present disclosure.

FIG. 2A illustrates an example 200-a that supports aspects of the present disclosure. In the example 200-a, the robotic system 201 may include a robot 214 (e.g., electronic and mechanical components including robotic arm 216), a navigation system (e.g., including a measurement device 238), a movable base 212, and a table 226 (e.g., a surgical table, an operating table, a patient bed, etc.).

The robotic system 201 (e.g., robot 214, robotic arm 216, table 226, measurement device 238, etc.) may include examples of aspects of like elements described herein with reference to FIG. 1. In some cases, the robotic system 201 may be referred to as a workstation. For example, the robotic system 201 may include a display 242 and additional user interfaces (e.g., keyboard, mouse, controls, etc.) for manipulating the robot 214.

The robotic system 201 and the measurement device 238 may support a non-rigid connection between the robot 114 and a patient 204. In an example, the non-rigid connection may be implemented using the measurement device 238. The measurement device 238 may be, for example, a mechanical arm coupled to the robotic system 201 (e.g., mechanically coupled to or integrated with the robot 214). The measurement device 238 may be or may be incorporated as part of a portable coordinate measuring machine supportive of precise measurements of an object (e.g., anatomical element 208) with respect to a multi-dimensional (e.g., three dimensional) coordinate system. The measurement device 238 may move within the multi-dimensional coordinate system, for example, forward/backward, up/down, and left/right, combined with rotational movement about three perpendicular axes. Information or data associated with movement of the measurement device 238 (e.g., movement of an object, as recorded and provided by the measurement device 238) may be vectorial (e.g., six DoF).

In some aspects, the measurement device 238 may include one or more components (e.g., connectors, arms, articulation points, joints, probes, etc.) supportive of bending, flexion, and/or movement of the measurement device 238. The measurement device 238 may freely bend and/or move (e.g., via bending at one or more joints or articulation points of the measurement device 238) in association with maintaining the non-rigid connection. The measurement device 238 may provide relatively minimal resistance (e.g., below a threshold resistance) supportive of the bending, flexion, and/or movement.

In some aspects, the measurement device 238 may be a high accuracy mechanical measurement device based on the robot. The measurement device 238 may be attached to the patient 204 via coupling component 246. The coupling component 246 may be, for example, a clamp, a pin, a rod, a screw (e.g., Schanz screw), or the like.

Aspects of the robotic system 201 may support monitoring of patient movement (e.g., as provided by the measurement device 238). In an example, the robotic system 201 may monitor patient movement (e.g., movement of the anatomical element 208) with respect to the robotic system 201. In some examples, the robotic system 201 may monitor patient movement with respect to the robot 214, the robotic arm 216, and/or a surgical tool coupled to the robotic arm 216.

In some aspects, the robotic system 201 may utilize the patient movement information in association with positioning the robotic arm 216, an end effector of the robotic arm 216, and/or a surgical tool coupled to the robotic arm 216. For example, the robotic system 201 may calibrate movement of the robotic arm 216, the surgical tool, and/or the end effector corresponding to the patient movement information so as to maintain a target accuracy. In some examples, the patient movement information may be vectorial. For example, the robotic system 201 may support monitoring patient movement and controlling the robotic arm 216, the surgical tool, and end effector according to multiple degrees of freedom (e.g., six DoF).

In some aspects, the robotic system 201 may initiate a new registration process for cases in which a relatively large movement (e.g., of the patient 204, the anatomical element 208, the surgical table 226, etc.) exceeds a threshold displacement value "d1". The threshold displacement value "d1" may be with respect to any axis (e.g., X-axis, Y-axis, Z-axis) of the environment of example 200-a. In an example, if the robotic system 201 detects that a movement (e.g., of the patient 204, the anatomical element 208, the surgical table 226, etc.) exceeds the threshold displacement value "d1", the robotic system 201 may generate and output an alert (e.g., an audio, visual, and/or haptic notification) indicating the need for a new registration process. The robotic system 201 may perform the new registration process autonomously or semi-autonomously (e.g., based in part on a user input).

In some aspects, the threshold displacement value "d1" may be based on (e.g., equal to, less than) a displacement between a reference position (e.g., a registered position) of the anatomical element 208 and a measured position of the anatomical element 208 that necessitates a new registration process. The robotic system 201 may generate and output an alert (e.g., audible, visual, haptic, etc.) or notification when the threshold displacement value "d1" is exceeded. In an example, the robotic system 201 may perform a new registration process when the threshold displacement value "d1" is exceeded.

Additionally, or alternatively, the robotic system 201 may initiate a new registration process for cases in which a parameter value (e.g., force, acceleration, velocity, etc.) measured by the measurement device 238 exceeds a corresponding threshold value (e.g., a threshold force value, a threshold acceleration value, a threshold velocity, etc.). For example, the robotic system 201 may initiate a new registration process when a measured force (e.g., exerted on the patient 204, sensed at the measurement device 238, etc.) exceeds a threshold force value. In another example, the robotic system 201 may initiate a new registration process when a measured acceleration (e.g., of the patient 204, sensed at the measurement device 238, etc.) exceeds a threshold acceleration value. In some examples, the robotic system 201 may initiate a new registration process when a measured velocity (e.g., of the patient 204, sensed at the measurement device 238, etc.) exceeds a threshold velocity value.

The measurement device 238 may support features for automatically disconnecting from the patient 204 based on a set of criteria. For example, the measurement device 238 may include one or more coupling elements 250 (also referred to herein as mechanical attachments) capable of automatically disconnecting from the patient 204 based on the set of criteria. Additionally, or alternatively, the coupling elements 250 may be capable of disconnecting from each other based on the set of criteria.

In an example, coupling element 250-*a* may detach (e.g., disconnect) from coupling element 250-*b* when a measured force (e.g., exerted on the patient 204, sensed at the measurement device 238, etc.) exceeds a threshold force value. Additionally, or alternatively, the coupling element 250-*a* may automatically detach (e.g., disconnect) from the coupling element 250-*b* when a displacement (e.g., between the robotic system 201 and the anatomical element 208) exceeds a threshold displacement value "d2". In some aspects, the threshold displacement value "d2" may be based on (e.g., equal to, less than) a maximum extendable length of the measurement device 238.

In an alternative or additional example, coupling element 250-*a* may detach (e.g., disconnect) from coupling component 246 when the measured force exceeds the threshold force value. In another example, coupling element 250-*a* may detach (e.g., disconnect) from coupling component 246 when the displacement (e.g., between the robotic system 201 and the anatomical element 208) exceeds the threshold displacement value "d2".

The robotic system 201 may generate and output an alert (e.g., audible, visual, haptic, etc.) or notification when the measured force exceeds the threshold force value. In some aspects, the robotic system 201 may generate and output an alert or notification when the displacement (e.g., between the robotic system 201 and the anatomical element 208) exceeds the threshold displacement value "d2". In some other aspects, the robotic system 201 may generate and output an alert or notification when coupling element 250-*a* detaches from coupling component 246 or when coupling element 250-*a* detaches from coupling element 250-*b*. In an example, the robotic system 201 may perform a new registration process described herein, autonomously or semi-autonomously (e.g., based in part on a user input), after detecting that the coupling element 250-*a* is reattached to coupling component 246 (or after the coupling element 250-*a* is reattached to coupling element 250-*b*).

The measurement device 238 may include a detachment mechanism at the coupling element 250-*a*, the coupling component 246, and/or the coupling element 250-*b*. The detachment mechanism may be a mechanical component or an electromechanical component. In some aspects, the detachment mechanism may include a sensor capable of detecting an attachment and/or detachment between multiple components (e.g., coupling element 250-*a* and coupling component 246, coupling element 250-*a* and coupling element 250-*b*). In an example, the sensor may detect that coupling element 250-*a* has detached from coupling component 246, and the sensor may output a signal indicating the detachment to the robotic system 201. In response to receiving the signal, the robotic system 201 may generate and output an alert indicating the detachment. In some examples, the alert may indicate the need for a new registration process as described herein.

Figure 2B:
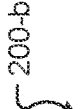
Figure 2C:
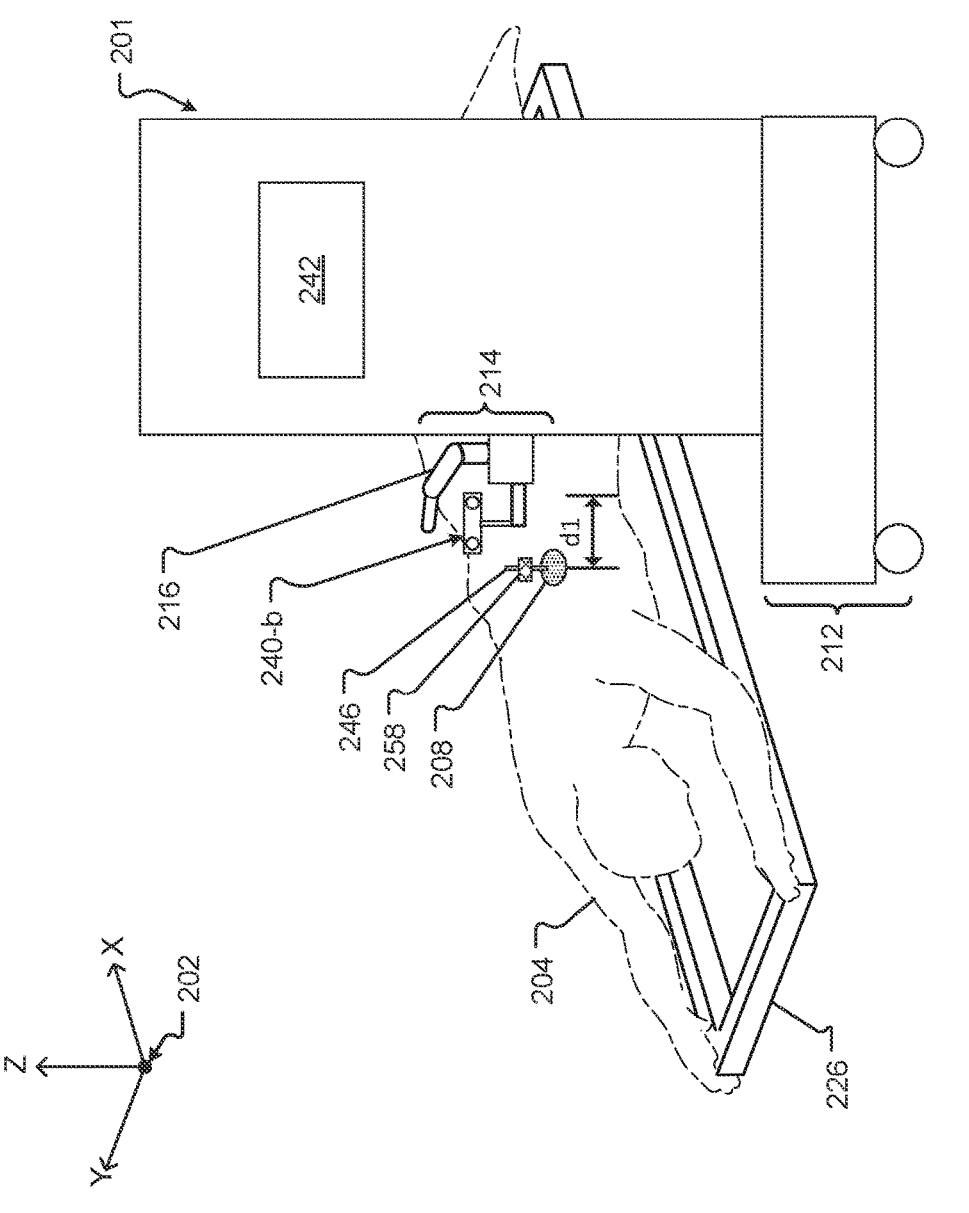
Figure 2D:
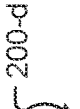
Figure 2D:
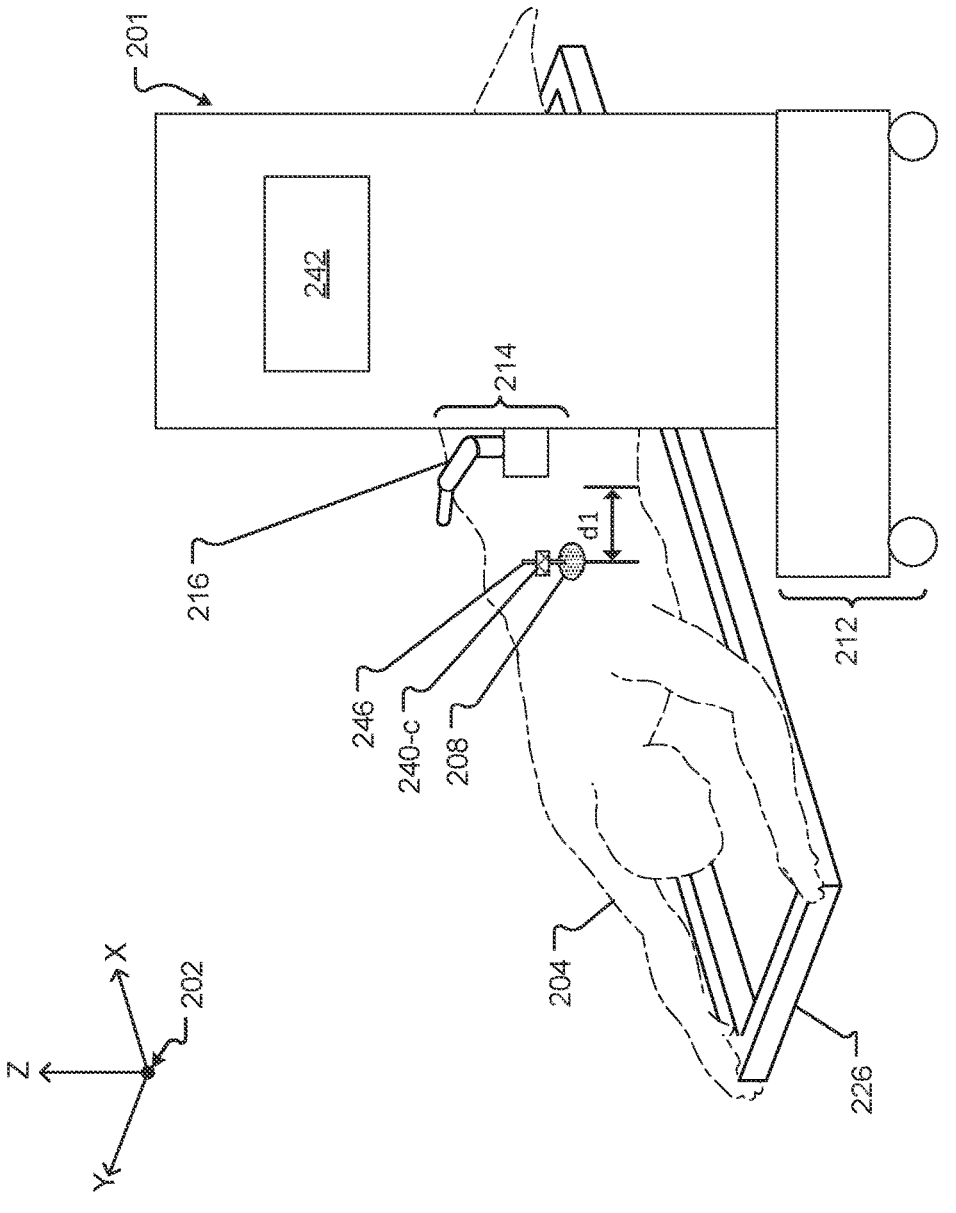

FIGS. 2B through 2D illustrate examples 200-*b* through 200-*d* that support aspects the present disclosure. In the examples 200-*b* through 200-*d*, alternative and/or additional aspects of the robotic system 201 may include a measurement device 240, aspects of which are described herein. Other features of the robotic system 201 (e.g., robot 214, robotic arm 216, table 226, etc.) may include examples of aspects of like elements described herein with reference to FIGS. 1 and 2A.

Referring to FIG. 2B, a measurement device 240-*a* may be, for example, a high accuracy optical measurement device coupled to the robotic system 201. For example, the measurement device 240-*a* may be mechanically coupled to or integrated with the robot 214. The measurement device 240-*a* may include one or more cameras (e.g., tracking cameras, imaging cameras, depth cameras, etc.). In another example, the measurement device 240-*a* may include one or more laser tracking devices.

In some aspects, the measurement device 240-*a* may track coordinates, position, and/or movement of a coupling element 246 (e.g., a Schanz screw) attached to the anatomical element 208. In some other aspects, the measurement device 240-*a* may track coordinates, position, and/or movement of a tracking device 254 attached to the anatomical element 208. In an example, the tracking device 254 may be attached to the anatomical element 208, for example, via a clamp, a pin, a rod, a screw (e.g., Schanz screw), or the like.

Referring to FIG. 2C, a measurement device 240-*b* may be, for example, a high accuracy acoustic measurement device.

In an example implementation, the measurement device 240-*b* may be mounted to the robotic system 201 (e.g., robot 214, robotic arm 216). The measurement device 240-*b* may include an ultrasonic sensor capable of tracking coordinates, position, and/or movement of the coupling element 246 (e.g., a Schanz screw) attached to the anatomical element 208. The ultrasonic sensor may include an acoustic transducer capable of transmitting and receiving ultrasonic signals (e.g., ultrasonic pulses). In an example, based on ultrasonic signals received from (e.g., reflected from) the coupling element 250, the measurement device 240-*b* may determine or calculate coordinates, position, and/or movement of the coupling element 250 (and thereby, the anatomical element 208). Additionally, or alternatively, the measurement device 240-*b* may determine or calculate coordinates, position, and/or movement of the anatomical element 208 based on ultrasonic signals transmitted toward and received from (e.g., reflected from) the anatomical element 208.

In another example implementation, the measurement device 240-*b* may include one or more sensors (e.g., microphones) capable of detecting and/or measuring ultrasonic signals (e.g., soundwaves) transmitted by a transmitting device 258. The transmitting device 258 may be attached to the patient, for example, via a clamp, a pin, a rod, a screw (e.g., Schanz screw), or the like, and the measurement device 240-*b* (e.g., sensors, microphones) may be mounted to the robotic system 201 (e.g., robot 214, robotic arm 216). Based on the signals output by the transmitting device 258, the measurement device 240-*b* may gather data (e.g., tracking data, positional data, movement data, etc.) in association with detecting the location of the patient 204 or the anatomical element 208.

Additionally, or alternatively, the measurement device 240-*b* may be attached to the patient 204, and the transmitting device 258 may be mounted to the robotic system 201. In an example, based on signals output by the transmitting device 258, the measurement device 240-*b* may determine the location of the patient 204 or the anatomical element 208 relative to the robotic system 201.

Referring to FIG. 2D, a measurement device 240-*c* may, for example, be capable of providing high accuracy acceleration measurements and/or rotational measurements. The measurement device 240-*c* may be attached to the patient (e.g., to the anatomical element 208), for example, via a clamp, a pin, a rod, a screw (e.g., Schanz screw), or the like. In an example, the measurement device 240-*c* may include an accelerometer. In another example, the measurement device 240-*c* may include a gyroscope. In some aspects, the measurement device 240-*c* may be a monolithic integrated multi-sensor (MIMS) device including a combination of sensors (e.g., an indirect interface sensor such as an accelerometer or gyroscope, a direct interface sensor such as a microphone, etc.).

In an example, the measurement device 240-c may transmit information (e.g., acceleration, rotation, acoustic signals, etc.) measured by the measurement device 240-c to the robotic system 201. Based on the information, the robotic system 201 may determine or calculate coordinates, position, and/or movement of the anatomical element 208.

Any quantity of the devices and systems described herein (e.g., robotic system 201, robot 214, robotic arm 216, measurement devices 240-a through 240-c, coupling components 246, tracking devices 254, transmitting devices 258, etc.) with reference to FIGS. 2A through 2D may be implemented in the robotic system 201.

Further, aspects described with reference to FIG. 2A may implemented by the examples described with reference to FIGS. 2B through 2D. For example, the robotic system 201 may support monitoring patient movement and controlling the robotic arm 216, the surgical tool, and end effector based on information provided by any of the measurement device 238 and the measurement device 240-a through 240-c. The robotic system 201 may calibrate movement of the robotic arm 216, the surgical tool, and/or the end effector corresponding to patient movement information determined using any of the measurement device 238 and the measurement device 240-a through 240-c (e.g., so as to maintain a target accuracy). The robotic system 201 may initiate a new registration process and/or generate an alert as described herein based on movement information as determined using any of the measurement device 238 and the measurement device 240-a through 240-c.

Figure 3:
FIG. 3 is an example of a process flow according to at least one implementation of the present disclosure.
Figure 3:
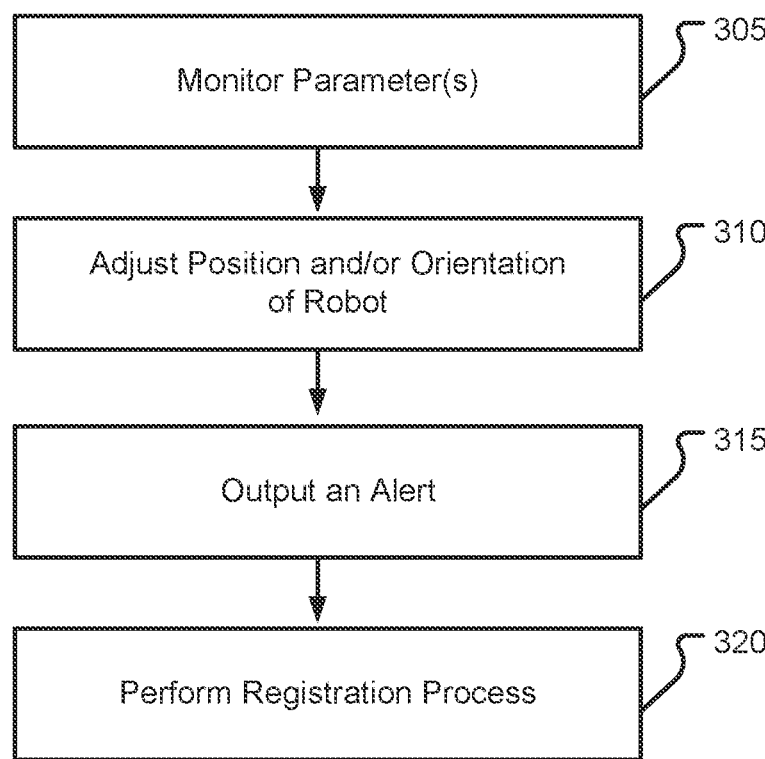

FIG. 3 illustrates an example of a process flow 300 in accordance with aspects of the present disclosure. In some examples, process flow 300 may implement aspects of a computing device 102, an imaging device 112, a robot 114, and/or a navigation system 118, described with reference to FIG. 1 and FIGS. 2A through 2D.

In the following description of the process flow 300, the operations may be performed in a different order than the order shown, or the operations may be performed in different orders or at different times. Certain operations may also be left out of the process flow 300, or other operations may be added to the process flow 300.

It is to be understood that any of the operations of process flow 300 may be performed by any device (e.g., a computing device 102, an imaging device 112, a robot 114, navigation system 118, etc.).

A robotic system includes a robot and one or more measurement devices. In some aspects, the robot is mounted to a movable base, and the robot includes one or more robotic arms.

At 305, the process flow 300 includes monitoring, by the one or more measurement devices, one or more parameters associated with an object. In some aspects, the object may include an anatomical element. In some aspects, the one or more parameters may include at least one of movement information, positional information, and orientation information associated with the object.

At 310, the process flow 300 includes adjusting a pose of the robot based on the one or more parameters satisfying one or more criteria.

In some aspects, adjusting the pose of the robot may include adjusting a position of the robot or a position of the one or more robotic arms. In some other aspects, adjusting the pose of the robot may include adjusting an orientation of the robot or an orientation of the one or more robotic arms.

In some aspects, the one or more parameters may include positional information associated with the object; and the one or more criteria may include a displacement threshold with respect to reference positional information associated with the object.

At 315, the process flow 300 may include outputting an alert based on the one or more parameters satisfying one or more second criteria.

At 320, the process flow 300 may include performing a registration process associated with the object and the robot, based on the one or more parameters satisfying the one or more second criteria.

In some aspects, the one or more measurement devices may include: a mechanical measurement device coupled to the robot and the object. In some aspects, the mechanical measurement device maintains a non-rigid connection between the robot and the object.

In some aspects, the mechanical measurement device may include one or more coupling elements configured to detach based on at least one of: a first force value measured at the object, a second force value measured at a portion of the mechanical measurement device, or both; and a displacement value of the object exceeding a threshold displacement value. In some aspects, the displacement value is measured by the mechanical measurement device.

In some other aspects, the one or more measurement devices may include one or more optical measurement devices. In some aspects, the one or more optical measurement devices are coupled to the robot, the one or more robotic arms, or both.

In some aspects, the one or more measurement devices may include at least one of: a first acoustic transducer coupled to the robot or the one or more robotic arms; and a second acoustic transducer coupled to the object.

In some aspects, the one or more measurement devices may include: a multi-sensor device coupled to the object. In some aspects, the multi-sensor device is a MIMS device including at least one of: a gyroscope; and an accelerometer.

The process flow 300 (and/or one or more operations thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the process flow 300. The at least one processor may perform operations of the process flow 300 by executing elements stored in a memory such as the memory 106. The elements stored in memory and executed by the processor may cause the processor to execute one or more operations of a function as shown in the process flow 300. One or more portions of the process flow 300 may be performed by the processor executing any of the contents of memory, such as image processing 120, segmentation 122, transformation 124, and/or registration 128.

As noted above, the present disclosure encompasses methods with fewer than all of the operations identified in FIG. 3 (and the corresponding description of the process flow 300), as well as methods that include additional operations beyond those identified in FIG. 3. The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, implementations, and/or configurations for the purpose of streamlining the disclosure. The features of the aspects, implementations, and/or configurations of the disclosure may be combined in alternate aspects, implementations, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, implementation, and/or configuration. Thus, the following claims are hereby incorporated into this Detailed Description, with each claim standing on its own as a separate preferred implementation of the disclosure.

Moreover, though the foregoing has included description of one or more aspects, implementations, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, implementations, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

Example Aspects of the Present Disclosure Include

A system including: a robot mounted to a movable base, the robot including one or more robotic arms; one or more measurement devices; a processor; and memory in electronic communication with the processor; and instructions stored in the memory, the instructions being executable by the processor to: monitor, by the one or more measurement devices, one or more parameters associated with an object; and adjust a pose of the robot based on the one or more parameters satisfying one or more criteria.

Any of the aspects herein, wherein adjusting the pose of the robot includes at least one of: adjusting a position of the robot or a position of the one or more robotic arms; and adjusting an orientation of the robot or an orientation of the one or more robotic arms, or both.

Any of the aspects herein, wherein the instructions are further executable by the processor to at least one of: output an alert based on the one or more parameters satisfying one or more second criteria; and perform a registration process associated with the object and the robot, based on the one or more parameters satisfying the one or more second criteria.

Any of the aspects herein, wherein the one or more parameters include at least one of movement information, positional information, and orientation information associated with the object.

Any of the aspects herein, wherein: the one or more parameters include positional information associated with the object; and the one or more criteria include a displacement threshold with respect to reference positional information associated with the object.

Any of the aspects herein, wherein the one or more measurement devices include a mechanical measurement device coupled to the robot and the object.

Any of the aspects herein, wherein the mechanical measurement device maintains a non-rigid connection between the robot and the object.

Any of the aspects herein, wherein: the mechanical measurement device includes one or more coupling elements configured to detach based on at least one of: a first force value measured at the object, a second force value measured at a portion of the mechanical measurement device, or both; and a displacement value of the object exceeding a threshold displacement value, wherein the displacement value is measured by the mechanical measurement device.

Any of the aspects herein, wherein the one or more measurement devices include one or more optical measurement devices, wherein the one or more optical measurement devices are coupled to the robot, the one or more robotic arms, or both.

Any of the aspects herein, wherein the one or more measurement devices include at least one of: a first acoustic transducer coupled to the robot or the one or more robotic arms; and a second acoustic transducer coupled to the object.

Any of the aspects herein, wherein the one or more measurement devices include a multi-sensor device coupled to the object.

Any of the aspects herein, wherein the multi-sensor device is a monolithic integrated multi-sensor (MIMS) device including at least one of: a gyroscope; and an accelerometer.

Any of the aspects herein, wherein the object includes an anatomical element.

An apparatus including: a robot, the robot including one or more robotic arms; a movable base coupled to the robot; one or more measurement devices; a processor; and memory in electronic communication with the processor; and instructions stored in the memory, the instructions being executable by the processor to: monitor, by the one or more measurement devices, one or more parameters associated with an object; and adjust a pose of the robot based on the one or more parameters satisfying one or more criteria.

Any of the aspects herein, wherein the one or more measurement devices include a mechanical measurement device coupled to the robot and the object.

Any of the aspects herein, wherein the mechanical measurement device maintains a non-rigid connection between the robot and the object.

Any of the aspects herein, wherein the mechanical measurement device includes one or more coupling elements configured to detach based on at least one of: a first force value measured at the object, a second force value measured at a portion of the mechanical measurement device, or both; and a displacement value of the object exceeding a threshold displacement value, wherein the displacement value is measured by the mechanical measurement device.

Any of the aspects herein, wherein the one or more measurement devices include at least one of: one or more optical measurement devices, wherein the one or more optical measurement devices are coupled to the robot, the one or more robotic arms, or both; one or more acoustic transducers, wherein the one or more acoustic transducers are coupled to the robot, the one or more robotic arms, the object, or a combination thereof; and a multi-sensor device coupled to the object.

A method including: monitoring, by one or more measurement devices of a robot, one or more parameters associated with an object; and adjusting a pose of the robot based on the one or more parameters satisfying one or more criteria, wherein the robot is mounted to a movable base.

Any of the aspects herein, further including: outputting an alert based on the one or more parameters satisfying one or more second criteria; and performing a registration process associated with the object and the robot, based on the one or more parameters satisfying the one or more second criteria.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/implementations in combination with any one or more other aspects/features/implementations.

Use of any one or more of the aspects or features as disclosed herein.

It is to be appreciated that any feature described herein can be claimed in combination with any other feature(s) as described herein, regardless of whether the features come from the same described implementation.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an implementation that is entirely hardware, an implementation that is entirely software (including firmware, resident software, micro-code, etc.) or an implementation combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

What is claimed is:

1. A system, comprising:
a robot mounted to a base that is movable relative to a patient, the robot comprising one or more robotic arms;
a first mechanical attachment to connect to an anatomical element of the patient, a second mechanical attachment to detachably connect to a first end of the first mechanical attachment, and a third mechanical attachment that enables a non-rigid connection between the second mechanical attachment and the robot;
a processor;
a memory in electronic communication with the processor; and
instructions stored in the memory, the instructions being executable by the processor to cause the processor to:
monitor one or more parameters associated with movement of or force exerted on the anatomical element;
determine, during the monitoring, that the one or more parameters satisfy one or more criteria associated with the movement of or the force exerted on the anatomical element; and
control, in response to the determination:
the second mechanical attachment to detach from the first mechanical attachment; and
a pose of the robot to be adjusted relative to the patient.

2. The system of claim 1, wherein controlling the pose of the robot to be adjusted comprises at least one of:
adjusting a position of the robot or a position of the one or more robotic arms; and
adjusting an orientation of the robot or an orientation of the one or more robotic arms, or both.

3. The system of claim 1, wherein the instructions are further executable by the processor to at least one of:
output an alert based on the one or more parameters satisfying one or more second criteria; and
perform a registration process associated with the anatomical element and the robot based on the one or more parameters satisfying the one or more second criteria.

4. The system of claim 1, wherein:

the one or more parameters comprise at least one of movement information, positional information, and orientation information associated with the anatomical element.

5. The system of claim 1, wherein:

the one or more parameters comprise positional information associated with the anatomical element; and the one or more criteria comprise a displacement threshold with respect to reference positional information associated with the anatomical element.

6. The system of claim 1, wherein the first mechanical attachment remains connected to the anatomical element after detaching from the second mechanical attachment.

7. The system of claim 1, further comprising:

one or more optical measurement devices, wherein the one or more optical measurement devices are coupled to the robot, the one or more robotic arms, or both.

8. The system of claim 1, further comprising at least one of:

a first acoustic transducer coupled to the robot or the one or more robotic arms; and a second acoustic transducer coupled to the anatomical element.

9. The system of claim 1, further comprising:

a multi-sensor device coupled to the anatomical element.

10. The system of claim 9, wherein the multi-sensor device is a monolithic integrated multi-sensor (MIMS) device comprising at least one of:

a gyroscope; and an accelerometer.

11. The system of claim 1, wherein the second mechanical attachment is further coupled with at least one robotic arm of the one or more robotic arms, and wherein the instructions are further executable by the processor to:

detect that the first mechanical attachment has been reattached with the second mechanical attachment; and automatically perform a registration between the anatomical element and the at least one robotic arm upon detecting that the first mechanical attachment has been reattached with the second mechanical attachment.

12. An apparatus, comprising:

a robot, the robot comprising one or more robotic arms;

a movable base coupled to the robot to enable movement of the robot relative to a patient;

a first mechanical attachment to connect to an anatomical element of the patient, a second mechanical attachment to detachably connect to a first end of the first mechanical attachment, and a third mechanical attachment that enables a non-rigid connection between the second mechanical attachment and the robot;

a processor;

a memory in electronic communication with the processor; and instructions stored in the memory, the instructions being executable by the processor to:

monitor one or more parameters associated with movement of or force exerted on the anatomical element;

determine, during the monitoring, that the one or parameters satisfy one or more criteria associated with the movement of or the force exerted on the anatomical element; and control, in response to the determination:

the second mechanical attachment to detach from the first mechanical attachment; and a pose of the robot to be adjusted relative to the patient.

13. The apparatus of claim 12, wherein the first mechanical attachment remains connected to the anatomical element after detaching from the second mechanical attachment, and wherein the second mechanical attachment is further configured to detach from the first mechanical attachment when a second force value measured at the anatomical element exceeds a second threshold force value.

14. The apparatus of claim 12, further comprising at least one of:

one or more optical measurement devices, wherein the one or more optical measurement devices are coupled to the robot, the one or more robotic arms, or both;

one or more acoustic transducers, wherein the one or more acoustic transducers are coupled to the robot, the one or more robotic arms, the anatomical element, or a combination thereof; and a multi-sensor device coupled to the anatomical element.

* * * * *